(12) United States Patent
Jansen et al.

(10) Patent No.: US 10,350,022 B2
(45) Date of Patent: Jul. 16, 2019

(54) ACETABULAR CUP IMPACTING USING PATIENT-SPECIFIC INSTRUMENTATION

(71) Applicant: ZIMMER, INC., Warsaw, IN (US)

(72) Inventors: Herbert Andre Jansen, Montreal (CA); Di Li, LaSalle (CA); Karine Duval, Montreal (CA); Bruno Falardeau, Montreal (CA); Francois Paradis, Boucherville (CA); Benoit Pelletier, Montreal (CA)

(73) Assignee: ZIMMER, INC., Warsaw, IN (US)

( * ) Notice: Subject to any disclaimer, the term of this patent is extended or adjusted under 35 U.S.C. 154(b) by 693 days.

(21) Appl. No.: 14/700,882

(22) Filed: Apr. 30, 2015

(65) Prior Publication Data
US 2015/0313723 A1   Nov. 5, 2015

Related U.S. Application Data

(60) Provisional application No. 61/986,515, filed on Apr. 30, 2014.

(51) Int. Cl.
*A61F 2/46* (2006.01)
*A61B 90/11* (2016.01)
(Continued)

(52) U.S. Cl.
CPC ............. *A61B 90/11* (2016.02); *A61B 90/13* (2016.02); *A61B 90/30* (2016.02); *A61F 2/4609* (2013.01);
(Continued)

(58) Field of Classification Search
CPC ..... A61B 17/1746; A61B 90/11; A61B 90/13; A61B 90/30; A61B 2090/395;
(Continued)

(56) References Cited

U.S. PATENT DOCUMENTS

| 4,841,975 A | 6/1989 | Woolson |
| 5,098,383 A | 3/1992 | Hemmy et al. |

(Continued)

FOREIGN PATENT DOCUMENTS

| AU | 2004293091 A1 | 6/2005 |
| AU | 2004293104 A1 | 6/2005 |

(Continued)

OTHER PUBLICATIONS

Taylor et al, "Computer-Integrated Surgery, Technology and Clinical Applications", The MIT Press, Cambridge, MA, London, UK, pp. 451-463.
(Continued)

*Primary Examiner* — Eric S Gibson
*Assistant Examiner* — Marcela I Shirsat
(74) *Attorney, Agent, or Firm* — Norton Rose Fulbright Canada LLP

(57) ABSTRACT

A cup impactor assembly comprises a shaft. A cup coupler is at a cup end of the shaft and is releasably connecting a cup in fixed relation. A handle is at an impacting end of the shaft. A visual guide is mounted to at least one of the shaft and the handle, the visual guide producing visual guidance for pointing at at least two landmarks of the pelvis or fixed relative to the pelvis, based on a pre-planned patient-specific relation between the at least two landmarks and a desired acetabular cup orientation relative to the landmarks. A method for orienting an acetabular cup prior to impacting in an acetabulum of a pelvis is also provided.

8 Claims, 9 Drawing Sheets

(51) Int. Cl.
*A61B 90/13* (2016.01)
*A61B 90/30* (2016.01)
A61B 90/00 (2016.01)
A61F 2/30 (2006.01)

(52) U.S. Cl.
CPC ..... *A61B 2090/395* (2016.02); *A61F 2/30942* (2013.01); *A61F 2002/4629* (2013.01); *A61F 2002/4681* (2013.01); *A61F 2002/4687* (2013.01); *A61F 2002/4696* (2013.01); *A61F 2002/4697* (2013.01)

(58) Field of Classification Search
CPC ...... A61F 2002/4623; A61F 2002/4629; A61F 2002/4681; A61F 2002/4687; A61F 2002/4697; A61F 2/4609; A61F 2/30942; A61F 2/34; A61F 2/4603; A61F 2002/4696
USPC ........................ 606/91, 87, 99, 102
See application file for complete search history.

(56) References Cited

U.S. PATENT DOCUMENTS

| | | | |
|---|---|---|---|
| 5,490,854 A | 2/1996 | Fisher et al. | |
| 5,768,134 A | 6/1998 | Swaelens et al. | |
| 5,871,018 A | 2/1999 | Delp et al. | |
| 5,916,219 A | 6/1999 | Matsuno et al. | |
| 7,357,057 B2 | 4/2008 | Chiang | |
| 7,468,075 B2 | 12/2008 | Lang et al. | |
| 7,510,557 B1 | 3/2009 | Bonutti | |
| 7,534,263 B2 | 5/2009 | Burdulis | |
| 7,618,451 B2 | 11/2009 | Berez et al. | |
| 7,634,119 B2 | 12/2009 | Tsougarakis et al. | |
| 7,717,956 B2 | 5/2010 | Lang | |
| 7,796,791 B2 | 9/2010 | Tsougarakis et al. | |
| 7,799,077 B2 | 9/2010 | Lang et al. | |
| 7,806,896 B1 | 10/2010 | Bonutti | |
| 7,806,897 B1 | 10/2010 | Bonutti | |
| 7,967,868 B2 | 6/2011 | White et al. | |
| 7,981,158 B2 | 7/2011 | Fitz et al. | |
| 8,062,302 B2 | 11/2011 | Lang et al. | |
| 8,066,708 B2 | 11/2011 | Lang et al. | |
| 8,070,752 B2 | 12/2011 | Metzger et al. | |
| 8,077,950 B2 | 12/2011 | Tsougarakis et al. | |
| 8,083,745 B2 | 12/2011 | Lang et al. | |
| 8,092,465 B2 | 1/2012 | Metzger et al. | |
| 8,094,900 B2 | 1/2012 | Steines et al. | |
| 8,105,330 B2 | 1/2012 | Fitz et al. | |
| 8,122,582 B2 | 2/2012 | Burdulis, Jr. et al. | |
| 8,133,234 B2 | 3/2012 | Meridew et al. | |
| 8,160,345 B2 | 4/2012 | Pavlovskaia et al. | |
| 8,175,683 B2 | 5/2012 | Roose | |
| 8,221,430 B2 | 7/2012 | Park et al. | |
| 8,234,097 B2 | 7/2012 | Steines et al. | |
| 8,241,293 B2 | 8/2012 | Stone et al. | |
| 8,282,646 B2 | 10/2012 | Schoenefeld et al. | |
| 8,298,237 B2 | 10/2012 | Schoenefeld | |
| 8,337,501 B2 | 12/2012 | Fitz et al. | |
| 8,337,507 B2 | 12/2012 | Lang et al. | |
| 8,343,218 B2 | 1/2013 | Lang et al. | |
| 8,366,771 B2 | 2/2013 | Burdulis et al. | |
| 8,377,129 B2 | 2/2013 | Fitz et al. | |
| 8,439,926 B2 | 5/2013 | Bojarski et al. | |
| 8,460,304 B2 | 6/2013 | Fitz et al. | |
| 8,480,754 B2 | 7/2013 | Bojarski et al. | |
| 8,500,740 B2 | 8/2013 | Bojarski et al. | |
| 8,529,568 B2 | 9/2013 | Bouadi | |
| 8,529,630 B2 | 9/2013 | Bojarski | |
| 8,585,708 B2 | 9/2013 | Fitz et al. | |
| 8,545,569 B2 | 10/2013 | Fitz et al. | |
| 8,551,099 B2 | 10/2013 | Lang | |
| 8,551,102 B2 | 10/2013 | Fitz et al. | |
| 8,551,103 B2 | 10/2013 | Fitz et al. | |
| 8,551,169 B2 | 10/2013 | Fitz et al. | |
| 8,556,906 B2 | 10/2013 | Fitz et al. | |
| 8,556,907 B2 | 10/2013 | Fitz et al. | |
| 8,556,971 B2 | 10/2013 | Lang | |
| 8,556,983 B2 | 10/2013 | Bojarski et al. | |
| 8,561,278 B2 | 10/2013 | Fitz et al. | |
| 8,562,611 B2 | 10/2013 | Fitz et al. | |
| 8,562,618 B2 | 10/2013 | Fitz et al. | |
| 8,568,479 B2 | 10/2013 | Fitz et al. | |
| 8,568,480 B2 | 10/2013 | Fitz et al. | |
| 8,617,172 B2 | 12/2013 | Fitz et al. | |
| 8,617,242 B2 | 12/2013 | Philipp | |
| 8,623,026 B2 | 1/2014 | Wong et al. | |
| 8,634,617 B2 | 1/2014 | Tsougarakis et al. | |
| 8,638,998 B2 | 1/2014 | Steines et al. | |
| 8,641,716 B2 | 2/2014 | Fitz et al. | |
| 8,657,827 B2 | 2/2014 | Fitz et al. | |
| 8,682,052 B2 | 3/2014 | Fitz et al. | |
| 2003/0055502 A1 | 3/2003 | Lang et al. | |
| 2003/0216669 A1 | 11/2003 | Lang et al. | |
| 2004/0073225 A1 | 4/2004 | Subba Rao | |
| 2004/0133276 A1 | 7/2004 | Lang et al. | |
| 2004/0138754 A1 | 7/2004 | Lang et al. | |
| 2004/0147927 A1 | 7/2004 | Tsougarakis et al. | |
| 2004/0153079 A1 | 8/2004 | Tsougarakis et al. | |
| 2004/0204644 A1 | 10/2004 | Tsougarakis et al. | |
| 2004/0204760 A1 | 10/2004 | Fitz et al. | |
| 2004/0236424 A1 | 11/2004 | Berez et al. | |
| 2005/0234461 A1 | 10/2005 | Burdulis et al. | |
| 2005/0267584 A1 | 12/2005 | Burdulis et al. | |
| 2006/0100504 A1 | 5/2006 | Jansen et al. | |
| 2006/0111722 A1 | 5/2006 | Bouadi | |
| 2007/0083266 A1 | 4/2007 | Lang | |
| 2007/0100462 A1 | 5/2007 | Lang et al. | |
| 2007/0156171 A1 | 7/2007 | Lang et al. | |
| 2007/0157783 A1 | 7/2007 | Chiang | |
| 2007/0198022 A1 | 8/2007 | Lang et al. | |
| 2007/0226986 A1 | 10/2007 | Park et al. | |
| 2007/0233141 A1 | 10/2007 | Park et al. | |
| 2007/0233269 A1 | 10/2007 | Steines et al. | |
| 2007/0250169 A1 | 10/2007 | Lang | |
| 2008/0114370 A1 | 5/2008 | Schoenefeld | |
| 2008/0147072 A1 | 6/2008 | Park et al. | |
| 2008/0161815 A1 | 7/2008 | Schoenefeld et al. | |
| 2008/0195216 A1 | 8/2008 | Philipp | |
| 2008/0243127 A1 | 10/2008 | Lang et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1 | 11/2008 | Kunz et al. | |
| 2009/0024131 A1 | 1/2009 | Metzgu et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1 | 4/2009 | Aram et al. | |
| 2009/0093816 A1 | 4/2009 | Roose et al. | |
| 2009/0099567 A1 | 4/2009 | Zajac | |
| 2009/0099665 A1* | 4/2009 | Taylor | A61F 2/34 623/22.21 |
| 2009/0110498 A1 | 4/2009 | Park et al. | |
| 2009/0131941 A1 | 5/2009 | Park et al. | |
| 2009/0131942 A1 | 5/2009 | Aker et al. | |
| 2009/0138020 A1 | 5/2009 | Park et al. | |
| 2009/0157083 A1 | 6/2009 | Park et al. | |
| 2009/0222014 A1 | 9/2009 | Bojarski et al. | |
| 2009/0222016 A1 | 9/2009 | Park et al. | |
| 2009/0222103 A1 | 9/2009 | Fitz et al. | |
| 2009/0226068 A1 | 9/2009 | Fitz et al. | |
| 2009/0228113 A1 | 9/2009 | Lang et al. | |
| 2009/0254093 A1 | 10/2009 | White et al. | |
| 2009/0270868 A1 | 10/2009 | Park et al. | |
| 2009/0276045 A1 | 11/2009 | Lang | |
| 2009/0306676 A1 | 12/2009 | Lang et al. | |
| 2009/0307893 A1 | 12/2009 | Burdulis, Jr. et al. | |
| 2009/0312805 A1 | 12/2009 | Lang et al. | |

(56) References Cited

U.S. PATENT DOCUMENTS

| | | |
|---|---|---|
| 2010/0023015 A1 | 1/2010 | Park |
| 2010/0042105 A1 | 2/2010 | Park et al. |
| 2010/0049195 A1 | 2/2010 | Park et al. |
| 2010/0054572 A1 | 3/2010 | Tsougarakis et al. |
| 2010/0076505 A1 | 3/2010 | Borja |
| 2010/0082035 A1 | 4/2010 | Keefer |
| 2010/0087829 A1 | 4/2010 | Metzger et al. |
| 2010/0152741 A1 | 6/2010 | Park et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0174376 A1 | 7/2010 | Lang et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217270 A1 | 8/2010 | Polinski et al. |
| 2010/0217338 A1 | 8/2010 | Carroll et al. |
| 2010/0228257 A1 | 9/2010 | Bonutti |
| 2010/0234849 A1 | 9/2010 | Bouadi |
| 2010/0249657 A1 | 9/2010 | Nycz et al. |
| 2010/0256479 A1 | 10/2010 | Park et al. |
| 2010/0262150 A1 | 10/2010 | Lian |
| 2010/0274534 A1 | 10/2010 | Steines et al. |
| 2010/0281678 A1 | 11/2010 | Burdulis, Jr. et al. |
| 2010/0286700 A1 | 11/2010 | Snider et al. |
| 2010/0298894 A1 | 11/2010 | Bojarski et al. |
| 2010/0303313 A1 | 12/2010 | Lang et al. |
| 2010/0303317 A1 | 12/2010 | Tsougarakis et al. |
| 2010/0303324 A1 | 12/2010 | Lang et al. |
| 2010/0305573 A1 | 12/2010 | Fitz et al. |
| 2010/0305574 A1 | 12/2010 | Fitz et al. |
| 2010/0305708 A1 | 12/2010 | Lang et al. |
| 2010/0305907 A1 | 12/2010 | Fitz et al. |
| 2010/0329530 A1 | 12/2010 | Lang et al. |
| 2011/0015636 A1 | 1/2011 | Katrana et al. |
| 2011/0015637 A1 | 1/2011 | De Smedt et al. |
| 2011/0015639 A1 | 1/2011 | Metzger et al. |
| 2011/0029091 A1 | 2/2011 | Bojarski et al. |
| 2011/0029093 A1 | 2/2011 | Bojarski et al. |
| 2011/0040168 A1 | 2/2011 | Arnaud et al. |
| 2011/0054478 A1 | 3/2011 | Vanasse et al. |
| 2011/0060341 A1 | 3/2011 | Angibaud et al. |
| 2011/0066193 A1 | 3/2011 | Lang et al. |
| 2011/0066245 A1 | 3/2011 | Lang et al. |
| 2011/0071533 A1 | 3/2011 | Metzger et al. |
| 2011/0071581 A1 | 3/2011 | Lang et al. |
| 2011/0071645 A1 | 3/2011 | Bojarski et al. |
| 2011/0071802 A1 | 3/2011 | Bojarski et al. |
| 2011/0087332 A1 | 4/2011 | Bojarski et al. |
| 2011/0092977 A1 | 4/2011 | Salehi et al. |
| 2011/0093108 A1 | 4/2011 | Ashby et al. |
| 2011/0106093 A1 | 5/2011 | Romano et al. |
| 2011/0144760 A1 | 6/2011 | Wong et al. |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0190775 A1 | 8/2011 | Ure |
| 2011/0196377 A1 | 8/2011 | Hodorek et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213376 A1 | 9/2011 | Maxson et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0214279 A1 | 9/2011 | Park et al. |
| 2011/0218539 A1 | 9/2011 | Fitz et al. |
| 2011/0218545 A1 | 9/2011 | Catanzarite et al. |
| 2011/0218584 A1 | 9/2011 | Fitz et al. |
| 2011/0224674 A1* | 9/2011 | White ............... A61B 17/1617 606/91 |
| 2011/0230888 A1 | 9/2011 | Lang et al. |
| 2011/0238073 A1 | 9/2011 | Lang et al. |
| 2011/0245835 A1 | 10/2011 | Dodds et al. |
| 2011/0266265 A1 | 11/2011 | Lang |
| 2011/0295329 A1 | 12/2011 | Fitz et al. |
| 2011/0295378 A1 | 12/2011 | Bojarski et al. |
| 2011/0313423 A1 | 12/2011 | Lang et al. |
| 2011/0313424 A1 | 12/2011 | Bono et al. |
| 2011/0319897 A1 | 12/2011 | Lang et al. |
| 2011/0319900 A1 | 12/2011 | Lang et al. |
| 2012/0010711 A1 | 1/2012 | Antonyshyn et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0065640 A1 | 3/2012 | Metzger et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0093377 A1 | 4/2012 | Tsougarakis et al. |
| 2012/0101503 A1 | 4/2012 | Lang et al. |
| 2012/0109138 A1 | 5/2012 | Meridew et al. |
| 2012/0116203 A1 | 5/2012 | Vancraen et al. |
| 2012/0116562 A1 | 5/2012 | Agnihotri et al. |
| 2012/0123422 A1 | 5/2012 | Agnihotri et al. |
| 2012/0123423 A1 | 5/2012 | Fryman |
| 2012/0130382 A1 | 5/2012 | Iannotti et al. |
| 2012/0130687 A1 | 5/2012 | Otto et al. |
| 2012/0141034 A1 | 6/2012 | Iannotti et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0165820 A1 | 6/2012 | De Smedt et al. |
| 2012/0172884 A1 | 7/2012 | Zheng et al. |
| 2012/0191205 A1 | 7/2012 | Bojarski et al. |
| 2012/0191420 A1 | 7/2012 | Bojarski et al. |
| 2012/0192401 A1 | 8/2012 | Pavlovskaia et al. |
| 2012/0197260 A1 | 8/2012 | Fitz et al. |
| 2012/0197408 A1 | 8/2012 | Lang et al. |
| 2012/0201440 A1 | 8/2012 | Steines et al. |
| 2012/0209276 A1 | 8/2012 | Schuster |
| 2012/0209394 A1 | 8/2012 | Bojarski et al. |
| 2012/0215226 A1 | 8/2012 | Bonutti |
| 2012/0221008 A1 | 8/2012 | Carroll et al. |
| 2012/0226283 A1 | 9/2012 | Meridew et al. |
| 2012/0232669 A1 | 9/2012 | Bojarski et al. |
| 2012/0232670 A1 | 9/2012 | Bojarski et al. |
| 2012/0232671 A1 | 9/2012 | Bojarski |
| 2012/0239045 A1 | 9/2012 | Li |
| 2012/0245647 A1 | 9/2012 | Kunz et al. |
| 2012/0245699 A1 | 9/2012 | Lang et al. |
| 2012/0265208 A1 | 10/2012 | Smith |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289966 A1 | 11/2012 | Fitz et al. |
| 2012/0296337 A1 | 11/2012 | Fitz et al. |
| 2013/0018379 A1 | 1/2013 | Fitz et al. |
| 2013/0018380 A1 | 1/2013 | Fitz et al. |
| 2013/0018464 A1 | 1/2013 | Fitz et al. |
| 2013/0023884 A1 | 1/2013 | Fitz et al. |
| 2013/0024000 A1 | 1/2013 | Bojarski et al. |
| 2013/0030419 A1 | 1/2013 | Fitz et al. |
| 2013/0030441 A1 | 1/2013 | Fitz et al. |
| 2013/0053856 A1 | 2/2013 | Penenberg |
| 2013/0079781 A1 | 3/2013 | Fitz et al. |
| 2013/0079876 A1 | 3/2013 | Fitz et al. |
| 2013/0081247 A1 | 4/2013 | Fitz et al. |
| 2013/0096562 A1 | 4/2013 | Fitz et al. |
| 2013/0103363 A1 | 4/2013 | Lang et al. |
| 2013/0110471 A1 | 5/2013 | Lang et al. |
| 2013/0123792 A1 | 5/2013 | Fitz et al. |
| 2013/0184713 A1 | 7/2013 | Bojarski et al. |

(56) References Cited

U.S. PATENT DOCUMENTS

| | | |
|---|---|---|
| 2013/0197870 A1 | 8/2013 | Steines et al. |
| 2013/0211409 A1 | 8/2013 | Burdulis, Jr. et al. |
| 2013/0211410 A1 | 8/2013 | Landes et al. |
| 2013/0211531 A1 | 8/2013 | Steines et al. |
| 2013/0245803 A1 | 9/2013 | Lang |
| 2013/0253522 A1 | 9/2013 | Bojarski et al. |
| 2013/0267958 A1* | 10/2013 | Iannotti ............... A61B 90/06 606/87 |
| 2013/0289570 A1 | 10/2013 | Chao |
| 2013/0296874 A1 | 11/2013 | Chao |
| 2013/0297031 A1 | 11/2013 | Hafez |
| 2013/0317511 A1 | 11/2013 | Bojarski et al. |
| 2013/0331850 A1 | 12/2013 | Bojarski et al. |
| 2014/0005792 A1 | 1/2014 | Lang et al. |
| 2014/0029814 A1 | 1/2014 | Fitz et al. |
| 2014/0031722 A1 | 1/2014 | Li et al. |
| 2014/0031826 A1 | 1/2014 | Bojarski et al. |
| 2014/0039631 A1 | 2/2014 | Bojarski et al. |
| 2014/0058396 A1 | 2/2014 | Fitz et al. |
| 2014/0058397 A1 | 2/2014 | Fitz et al. |
| 2014/0066935 A1 | 3/2014 | Fitz et al. |
| 2014/0066936 A1 | 3/2014 | Fitz et al. |
| 2014/0074441 A1 | 3/2014 | Fitz et al. |
| 2014/0086780 A1 | 3/2014 | Miller et al. |
| 2014/0364858 A1* | 12/2014 | Li ...................... A61F 2/4609 606/91 |

FOREIGN PATENT DOCUMENTS

| | | |
|---|---|---|
| AU | 2005309692 A1 | 6/2006 |
| AU | 2005311558 A1 | 6/2006 |
| AU | 2002310193 B2 | 3/2007 |
| AU | 2006297137 A1 | 4/2007 |
| AU | 2002310193 B8 | 5/2007 |
| AU | 2007202573 A1 | 6/2007 |
| AU | 2007212033 A1 | 8/2007 |
| AU | 2007226924 A1 | 9/2007 |
| AU | 2009221773 A1 | 9/2009 |
| AU | 2009246474 A1 | 11/2009 |
| AU | 2010201200 A1 | 4/2010 |
| AU | 2011203237 A1 | 7/2011 |
| AU | 2010217903 A1 | 9/2011 |
| AU | 2010236263 A1 | 11/2011 |
| AU | 2010264466 A1 | 2/2012 |
| AU | 2010289706 A1 | 3/2012 |
| AU | 2010315099 A1 | 5/2012 |
| AU | 2010327987 A1 | 6/2012 |
| AU | 2011203237 B2 | 10/2012 |
| AU | 2012216829 A1 | 10/2012 |
| AU | 2012217654 A1 | 10/2013 |
| AU | 2007212033 B2 | 1/2014 |
| AU | 2014200073 A1 | 1/2014 |
| AU | 2012289973 A1 | 3/2014 |
| AU | 2012296556 A1 | 3/2014 |
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2804883 A1 | 6/2005 |
| CA | 2588907 A1 | 6/2006 |
| CA | 2590534 A1 | 6/2006 |
| CA | 2623834 A1 | 4/2007 |
| CA | 2641241 A1 | 8/2007 |
| CA | 2646288 A1 | 9/2007 |
| CA | 2717760 A1 | 9/2009 |
| CA | 2765499 A1 | 12/2010 |
| CA | 2771573 A1 | 3/2011 |
| CA | 2779283 A1 | 5/2011 |
| CA | 2782137 A1 | 6/2011 |
| CA | 2546965 C | 3/2013 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101384230 A | 3/2009 |
| CN | 101442960 A | 5/2009 |
| CN | 100502808 C | 6/2009 |
| CN | 102006841 A | 4/2011 |
| CN | 102125448 A | 7/2011 |
| CN | 102405032 A | 4/2012 |
| CN | 102448394 A | 5/2012 |
| CN | 101420911 B | 7/2012 |
| CN | 102599960 A | 7/2012 |
| CN | 102612350 A | 7/2012 |
| CN | 1913844 B | 9/2012 |
| CN | 102711670 A | 10/2012 |
| CN | 102724934 A | 10/2012 |
| CN | 102805677 A | 12/2012 |
| CN | 103153240 A | 6/2013 |
| CN | 1729483 B | 10/2013 |
| CN | 103476363 A | 12/2013 |
| DE | 60336002 | 3/2011 |
| DE | 60239674 | 5/2011 |
| DE | 602004032166 | 5/2011 |
| DE | 602005027391 | 5/2011 |
| EP | 1555962 A1 | 7/2005 |
| EP | 1558181 A1 | 8/2005 |
| EP | 1567985 A2 | 8/2005 |
| EP | 1575460 A2 | 9/2005 |
| EP | 1686930 A1 | 8/2006 |
| EP | 1686931 A1 | 8/2006 |
| EP | 1389980 A4 | 4/2007 |
| EP | 1814491 A1 | 8/2007 |
| EP | 1833387 A1 | 9/2007 |
| EP | 1686930 A4 | 10/2007 |
| EP | 1686931 A4 | 1/2008 |
| EP | 1928359 A2 | 6/2008 |
| EP | 1951136 A1 | 8/2008 |
| EP | 1981409 A2 | 10/2008 |
| EP | 1996121 A2 | 12/2008 |
| EP | 2114312 A2 | 11/2009 |
| EP | 2124764 A1 | 12/2009 |
| EP | 1928359 A4 | 10/2010 |
| EP | 2259753 A1 | 12/2010 |
| EP | 2265199 A1 | 12/2010 |
| EP | 1555962 B1 | 2/2011 |
| EP | 2292188 A2 | 3/2011 |
| EP | 2292189 A2 | 3/2011 |
| EP | 1389980 B1 | 4/2011 |
| EP | 1686930 B1 | 4/2011 |
| EP | 1833387 B1 | 4/2011 |
| EP | 2303193 A1 | 4/2011 |
| EP | 2316357 A1 | 5/2011 |
| EP | 2324799 A2 | 5/2011 |
| EP | 2335654 A1 | 6/2011 |
| EP | 2403434 A1 | 1/2012 |
| EP | 2405865 A2 | 1/2012 |
| EP | 2419035 A1 | 2/2012 |
| EP | 2265199 A4 | 3/2012 |
| EP | 2303193 A4 | 3/2012 |
| EP | 2259753 A4 | 4/2012 |
| EP | 2292188 A3 | 5/2012 |
| EP | 2292189 A3 | 5/2012 |
| EP | 2445451 A1 | 5/2012 |
| EP | 2470126 A1 | 7/2012 |
| EP | 2496183 A2 | 9/2012 |
| EP | 2509539 A2 | 10/2012 |
| EP | 2512381 A2 | 10/2012 |
| EP | 2324799 A3 | 1/2013 |
| EP | 2419035 A4 | 1/2013 |
| EP | 2445451 A4 | 3/2013 |
| EP | 2403434 A4 | 4/2013 |
| EP | 2591756 A1 | 5/2013 |
| EP | 2496183 A4 | 12/2013 |
| EP | 2512381 A4 | 12/2013 |
| EP | 2649951 A2 | 12/2013 |
| EP | 2649951 A3 | 12/2013 |
| EP | 2671520 A3 | 12/2013 |
| EP | 2671521 A3 | 12/2013 |
| EP | 2671522 A3 | 12/2013 |

(56) References Cited

FOREIGN PATENT DOCUMENTS

| | | |
|---|---|---|
| EP | 2114312 B1 | 1/2014 |
| EP | 2710967 A2 | 3/2014 |
| GB | 2484042 A | 3/2012 |
| GB | 2489884 A | 10/2012 |
| GB | 201213674 | 10/2012 |
| GB | 2484042 B | 3/2014 |
| HK | 1059882 A1 | 8/2011 |
| HK | 1072710 A1 | 8/2011 |
| HK | 1087324 A1 | 11/2011 |
| HK | 1104776 A1 | 11/2011 |
| JP | 2006510403 A | 3/2006 |
| JP | 2007514470 A | 6/2007 |
| JP | 2011519713 A | 7/2011 |
| JP | 2011224384 A | 11/2011 |
| JP | 2012091033 A | 5/2012 |
| JP | 2012176318 A | 9/2012 |
| JP | 5053515 B2 | 10/2012 |
| JP | 2012187415 A | 10/2012 |
| JP | 2012523897 A | 10/2012 |
| JP | 5074036 B2 | 11/2012 |
| JP | 2012531265 A | 12/2012 |
| JP | 2013503007 A | 1/2013 |
| JP | 5148284 B2 | 2/2013 |
| JP | 5198069 B2 | 5/2013 |
| JP | 2014000425 A | 1/2014 |
| KR | 20050072500 A | 7/2005 |
| KR | 20050084024 A | 8/2005 |
| KR | 20120090997 A | 8/2012 |
| KR | 20120102576 A | 9/2012 |
| MX | 2012007140 A | 1/2013 |
| NZ | 597261 A | 11/2013 |
| SG | 173840 A1 | 9/2011 |
| SG | 175229 A1 | 11/2011 |
| SG | 176833 A1 | 1/2012 |
| SG | 178836 A1 | 4/2012 |
| SG | 193484 A1 | 10/2013 |
| TW | 200509870 A | 3/2005 |
| TW | 1231755 B | 5/2005 |
| TW | 200800123 A | 1/2008 |
| TW | 1330075 B | 9/2010 |
| WO | 2004030556 A2 | 4/2004 |
| WO | 2004049981 A3 | 6/2004 |
| WO | 2004051301 A3 | 6/2004 |
| WO | 2005051239 A1 | 6/2005 |
| WO | 2005051240 A1 | 6/2005 |
| WO | 2006058057 A2 | 6/2006 |
| WO | 2006060795 A1 | 6/2006 |
| WO | 2006058057 A8 | 7/2006 |
| WO | 2007041375 A2 | 4/2007 |
| WO | 2007062103 A1 | 5/2007 |
| WO | 2007092841 A2 | 8/2007 |
| WO | 2007109641 A2 | 9/2007 |
| WO | 2007092841 A3 | 11/2007 |
| WO | 2007109641 A3 | 12/2007 |
| WO | 2008101090 A2 | 8/2008 |
| WO | 2008112996 A1 | 9/2008 |
| WO | 2008101090 A3 | 11/2008 |
| WO | 2008157412 A2 | 12/2008 |
| WO | 2007041375 A3 | 4/2009 |
| WO | 2008157412 A3 | 4/2009 |
| WO | 2009111626 A2 | 9/2009 |
| WO | 2009111639 A1 | 9/2009 |
| WO | 2009111656 A1 | 9/2009 |
| WO | 2009140294 A1 | 11/2009 |
| WO | 2009111626 A3 | 1/2010 |
| WO | 2010099231 A2 | 9/2010 |
| WO | 2010099353 A1 | 9/2010 |
| WO | 2010121147 A1 | 10/2010 |
| WO | 2010099231 A3 | 11/2010 |
| WO | 2011028624 A1 | 3/2011 |
| WO | 2011056995 A2 | 5/2011 |
| WO | 2011072235 A2 | 6/2011 |
| WO | 2011075697 A2 | 6/2011 |
| WO | 2011056995 A3 | 9/2011 |
| WO | 2011075697 A3 | 10/2011 |
| WO | 2011072235 A3 | 12/2011 |
| WO | 2012112694 A1 | 8/2012 |
| WO | 2012112694 A2 | 8/2012 |
| WO | 2012112698 A2 | 8/2012 |
| WO | 2012112701 A2 | 8/2012 |
| WO | 2012112702 A2 | 8/2012 |
| WO | 2012112694 A3 | 1/2013 |
| WO | 2012112701 A3 | 1/2013 |
| WO | 2012112702 A3 | 1/2013 |
| WO | 2013020026 A1 | 2/2013 |
| WO | 2013025814 A1 | 2/2013 |
| WO | 2012112698 A3 | 3/2013 |
| WO | 2013056036 A1 | 4/2013 |
| WO | 2013119790 A1 | 8/2013 |
| WO | 2013119865 A1 | 8/2013 |
| WO | 2013131066 A1 | 9/2013 |
| WO | 2013152341 A1 | 10/2013 |
| WO | 2013155500 A1 | 10/2013 |
| WO | 2013155501 A1 | 10/2013 |
| WO | 2014008444 A1 | 1/2014 |
| WO | 2014035991 A1 | 3/2014 |
| WO | 2014047514 A1 | 3/2014 |

OTHER PUBLICATIONS

Hofmann et al, "Natural-Knee II System", Intermedics Orthopedics, Austin, TX, 1995.

* cited by examiner

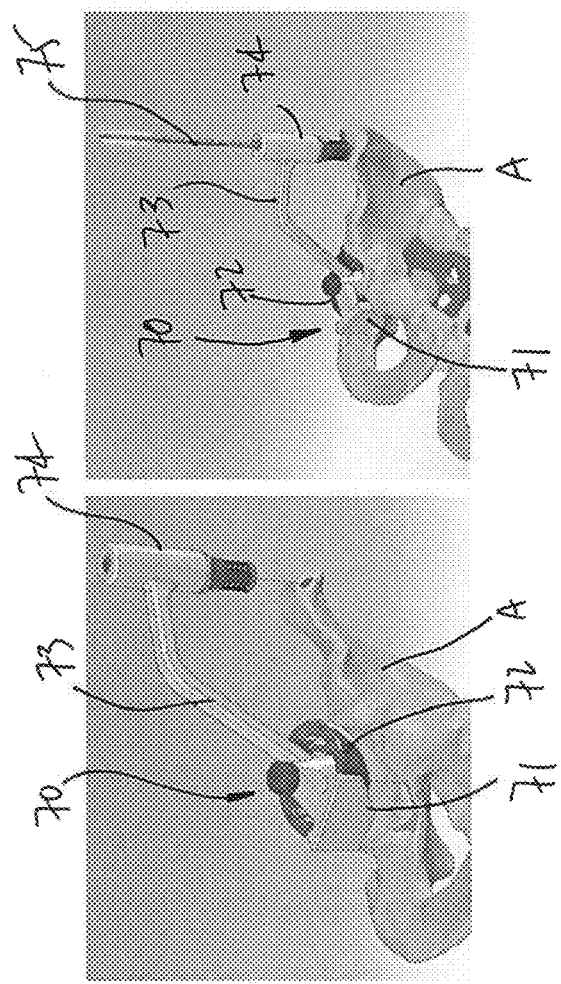
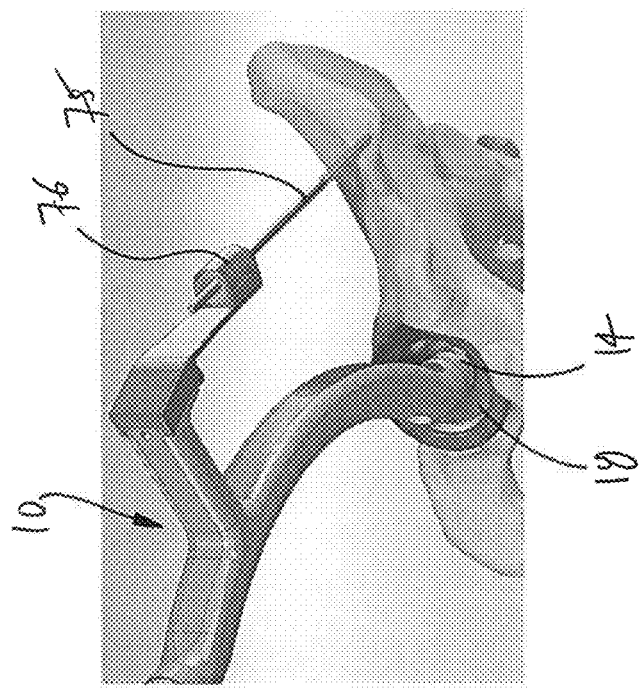
FIG. 7A
FIG. 7B
FIG. 7C

ACETABULAR CUP IMPACTING USING PATIENT-SPECIFIC INSTRUMENTATION

CROSS-REFERENCE TO RELATED APPLICATION

The present application claims priority on U.S. Provisional Patent Application No. 61/986,515, filed on Apr. 30, 2014, the contents of which are incorporated herein by reference.

TECHNICAL FIELD

The present application relates to hip surgery, and more particularly to a device and method for providing placement guidance during cup implanting.

BACKGROUND OF THE ART

In hip replacement surgery, a common procedure is to resurface the acetabulum to then place a cup therein. The implanted cup is typically interfaced with an implant head on the femur. The combination of the cup and the implant head replicate the hip joint, hence allowing movement of the femur relative to the pelvis. For this reason, the positioning of the cup implant in the acetabulum must be done with accuracy and precision. Indeed, the cup is preferably positioned according to given abduction and anteversion relative to the pelvis, to maximize a range of motion of the femur relative to the pelvis, to avoid leg length discrepancy, and to preserve the longevity of the hip joint implants.

Therefore, there has been devised numerous technologies to navigate the resurfacing of the acetabulum and the implanting of the cup therein, i.e., provide data to guide an operator in implanting the cup to a desired position and/or orientation. Cup impactors are conventionally used to forcefully insert the cup in the resurfaced acetabulum. Cup impactors are sturdy pieces of equipment impacted by an operator to drive the cup into the acetabulum. Depending on the tracking technology used to navigate the impacting movement (e.g., optical trackers being conventionally used), trackers are attached to the impactor to provide the operator with data pertaining to the position and/or orientation of the cup relative to the pelvis. However, systems using trackers typically require some calibration steps during the procedure, and other ways of approaching acetabular cup positioning would be desirable.

SUMMARY

It is an aim of the present disclosure to provide a novel cup impactor with patient-specific visual guide.

It is a further aim of the present disclosure to provide a method for navigating acetabular cup impacting using patient-specific instrumentation.

Therefore, in accordance with a first embodiment of the present disclosure, there is provided a method for orienting an acetabular cup prior to impacting in an acetabulum of a pelvis, comprising: obtaining a cup impactor with a visual guide thereon at a location based on pre-operative planning specific to the patient; releasably connecting an acetabular cup to an end of the cup impactor; seating the cup at the end of the cup impactor in the acetabulum; aligning the visual guide with at least two landmarks on the pelvis planned in the pre-operative planning specific to the patient by rotating the cup impactor with the cup seated in the acetabulum; and when the visual guide is aligned, impacting the cup into the acetabulum with the cup impactor.

In accordance with a second embodiment of the present disclosure, there is provided a cup impactor assembly comprising: a shaft; a cup coupler at a cup end of the shaft adapted to releasably connect a cup in fixed relation; a handle at an impacting end of the shaft; and a visual guide mounted to at least one of the shaft and the handle, the visual guide producing visual guidance for pointing at at least two landmarks of the pelvis or fixed relative to the pelvis, based on a pre-planned patient-specific relation between the at least two landmarks and a desired acetabular cup orientation relative to the landmarks.

DESCRIPTION OF THE DRAWINGS

FIGS. 7A-7C illustrate a method of using a cup impactor with a patient specific block in accordance with the method of FIG. 2 of the present disclosure.

DETAILED DESCRIPTION

Figure 1:
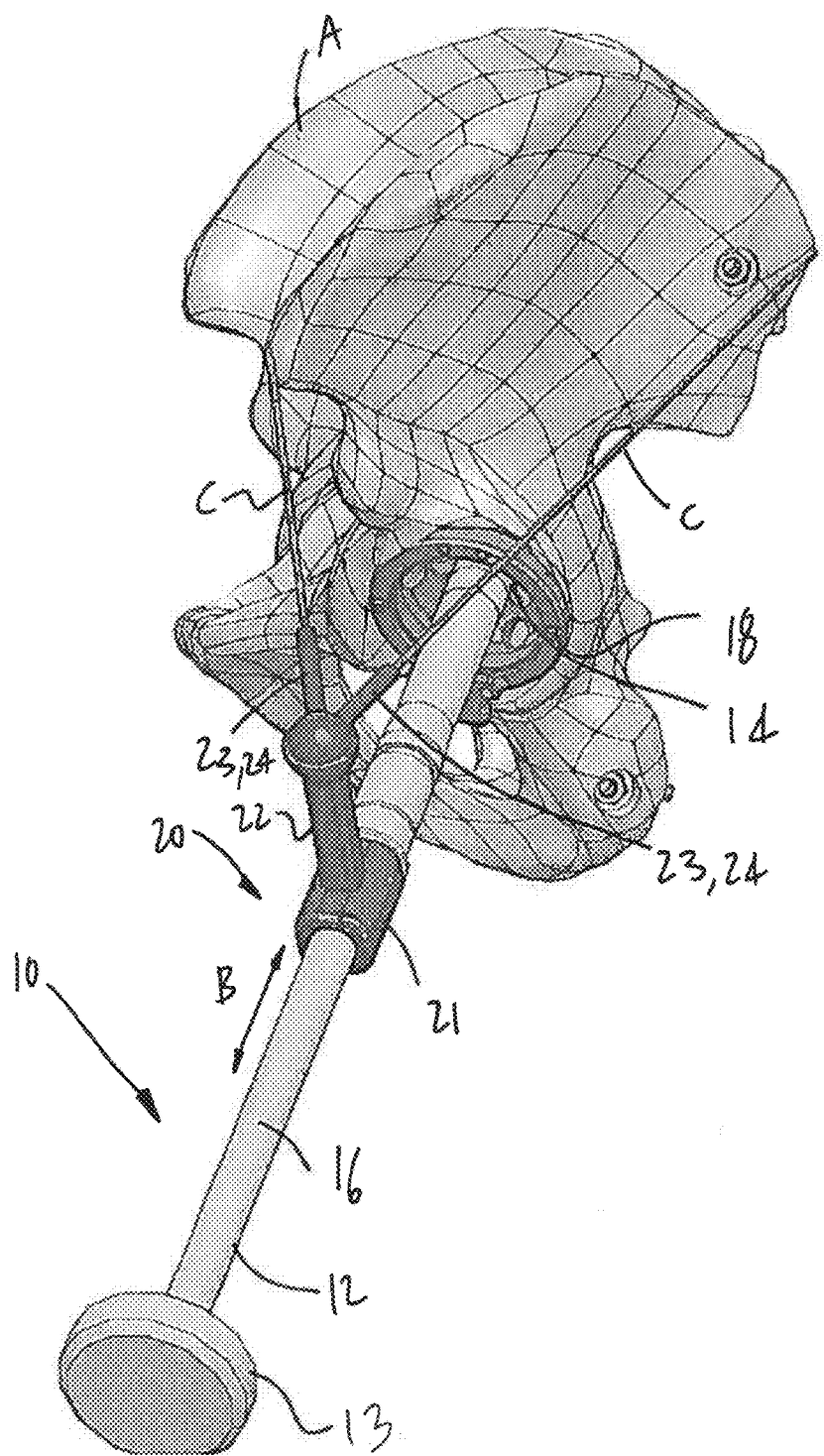
FIG. 1 is a perspective view of a cup impactor with visual guide in accordance with the present disclosure, relative to a pelvis.

Referring to the drawings and more particularly to FIG. 1, there is illustrated a cup impactor 10 equipped with a visual guide 20 in accordance with the present disclosure, rendering the assembly specific to the patient. More specifically, while the cup impactor 10 may be a generic cup impactor, the presence of the visual guide 20 thereon, which visual guide 20 has been specifically conceived and/or configured for the patient, renders the assembly patient-specific. Patient specific refers hereinafter to components that are fabricated in part or in whole based on anatomic data unique to the patient, obtained pre-operatively using imaging techniques, as detailed hereinafter. Accordingly, the cup impactor 10 may be accompanied by a file that includes the patient-specific relation between the anatomical landmarks and a desired acetabular cup orientation relative to the landmarks used for the fabrication of a patient-specific portion of the cup impactor 10. For instance, the file may be a virtual three-dimension model, vectorial information representative of geometrical data between landmarks and desired orientation, etc.

The cup impactor 10 illustrated in FIG. 1 is shown as having a handle 12 at the end of which is an impacting head 13. A cup coupler 14 is at an opposing end of the cup impactor 10, with the handle 12 and the cup coupler 14 being interrelated by an elongated shaft 16, with the handle 12 being part of the shaft 16 in the embodiment of FIG. 1. The shaft 16 is shown as being a straight shaft. However, other configurations are considered as well for the shaft 16, such as shaft with an offset section, etc, or with additional ergonomic features for being grasped, at the handle 12, as shown later on in embodiments of the cup impactor 10. The cup 18 is the frusto-spherical or hemispherical implant that is to be inserted in the acetabulum of the pelvis A. Various types of cups 18 may be used, including cups 18 subsequently requiring a liner in their cavity, etc. The cup coupler 14, which may have any common configuration, attaches to the cup 18 in a releasable fixed arrangement. For example, an axis of the shaft 16 may pass through the center of the cup 18, and the axis may also be normal to a plane of the rim of the cup 18. When the cup 18 is at the end of the cup coupler 14, the operator, holding on to the handle 12, may impact the impacting end 13 so as to drive the cup 18 into engagement in the acetabulum of the pelvis A. It is observed that the alignment of the shaft 16 during the impacting will have a direct impact on the orientation of the cup 18 in the pelvis A. Stated differently, the abduction and anteversion will depend on the orientation of the cup 18 once inserted in the pelvis A. It is therefore desired that the orientation of the shaft 16 be navigated just before the impacting and/or during the impacting, to guide the operator in driving the cup 18 in a desired orientation (i.e., to a desired abduction and anteversion).

For this purpose, the visual guide 20 is provided as a patient-specific guidance aid. According to one embodiment, shown in FIG. 1, the visual guide 20 has a sleeve 21 that is mounted to the shaft 16. It is also considered to have the sleeve 21 on the handle 12, or closer to the cup coupler 14. Moreover, other configurations are considered to hold the visual guide 20 to the cup impactor 10 as an alternative to the sleeve 21, including brackets with fasteners, projections on the cup impactor 10 and/or a combination of these possibilities. In an embodiment, the sleeve 21 may translate along the shaft 16 (forming a prismatic joint), as illustrated by B. It is contemplated to provide a biasing mechanism to ensure that the visual guide 20 returns to the position shown in FIG. 1. The translational degree of freedom of the prismatic joint arrangement would help the operator in evaluating the orientation of the cup 18 once implanted, before the cup 18 is fully implanted, as explained hereinafter.

A support 22 projects from the sleeve 21 in a direction generally transverse to the axis of the shaft 16. Arms 23 are at ends of the support 22 and each support a light source 24. The light sources 24 are of the type that can produce a visible linear light beam in the manner shown at C. The light sources 24 may be known as lasers, light pointers, laser pointers, coherent light emitters, etc and may typically be operated by batteries, or by any other power source. The visual guide 20 is configured, shaped and/or dimensioned taking into consideration a desired orientation of the cup 18, to point the light beams to two distinct landmarks on the pelvis A or associated with the pelvis A when the cup impactor 10 holds the cup 18 in the desired orientation of the cup 18. In the embodiment of FIG. 1, these landmarks may be the anterior superior iliac spine (ASIS) and the posterior superior iliac spine (PSIS), which are often visible when covered by skin due to their projecting shape and to the thinness of the skin, or which can easily be manually detected through skin.

It is observed from FIG. 1 that the light beams C lie in a plane in which the axis of the shaft 16 does not lie: that is a trigonometric condition for the assembly of the cup impactor 10 and the visual guide 20 to point to the two landmarks from the unique desired orientation of the shaft 16 when the cup 18 is in the acetabulum. While the visual guide 20 is shown as employing light sources 24 emitting light beams C, it is contemplated to use other technologies as well. For instance, the visual guide 20 may have a pair of rods projecting from the arms 23 of the support 22, which rods would be sized to have their free ends come into contact with the landmarks on the pelvis A.

Figure 2:
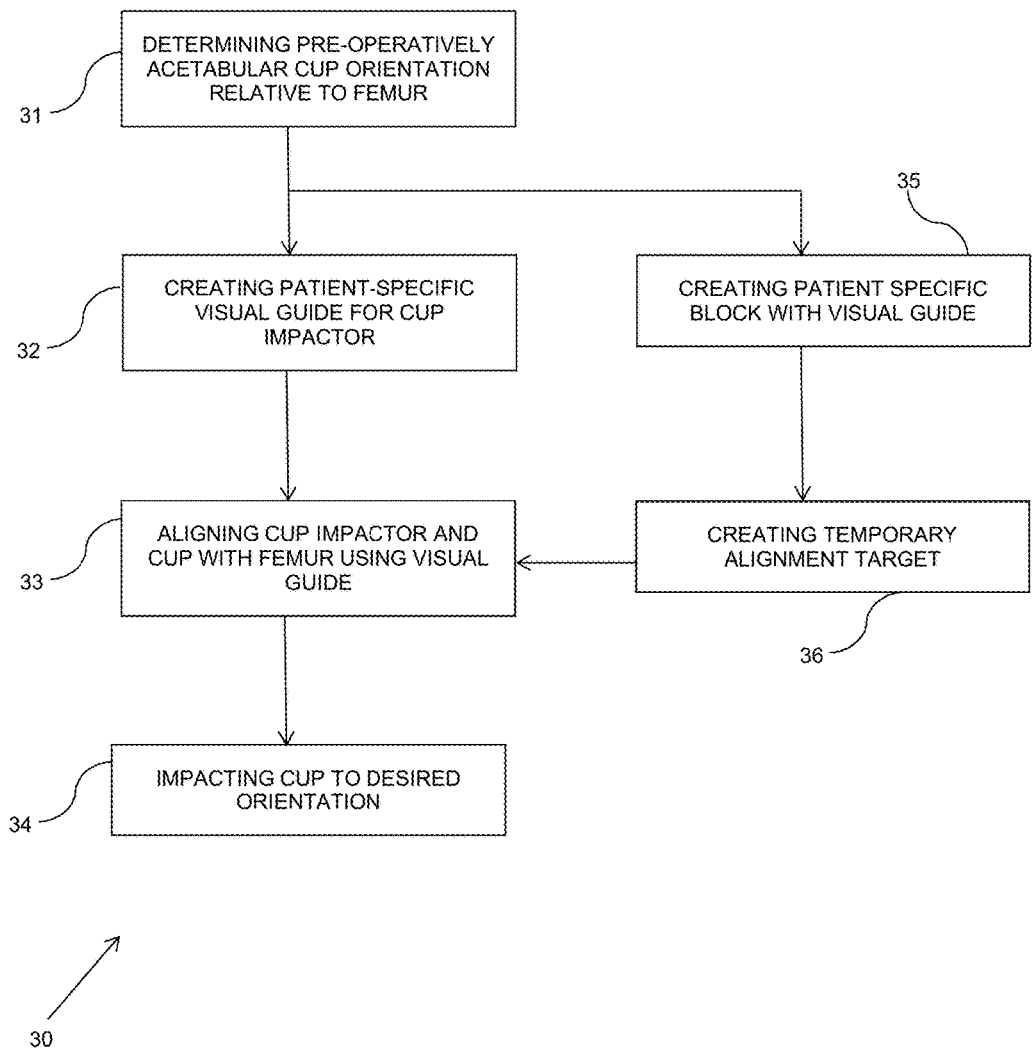
FIG. 2 is a flow chart illustrating a method for creating a patient-specific visual guide for cup impactor and method for impacting the cup to a desired orientation.

Referring concurrently to FIGS. 1 and 2, there is shown a method 30 for creating the patient-specific visual guide 20 for the cup impactor 10 (or like cup impactor), and for subsequently navigating the cup impactor 10 to reach a desired orientation of the cup 18. While reference is made to the cup impactor 10 of FIG. 1, the method 30 could be performed using other types of cup impactors or cup positioning devices, with other shapes of visual guides 20.

According to 31, a desired acetabular cup orientation is determined pre-operatively, relative to the femur A. In an embodiment, images of the patient's pelvis are used to determine the desired acetabular cup orientation. There are numerous ways to obtain these images, for instance by using X-rays taken from two standpoints, by using CT-scanning, by magnetic resonance, even by taking points manually using tracking technology. These imaging techniques may allow an operator to determine the cup orientation from a three-dimensional (3D) model representative of the patient's pelvis, and various techniques have been devised to model the pelvis in 3D with suitable precision. Using the images or model, an operator may determine the desired abduction and anteversion angles, as well as the center of rotation of the acetabulum, as part of a desired acetabular cup orientation. Moreover, using the images or 3D model, the operator establishes the position of the given landmarks (e.g., ASIS and PSIS as in FIG. 1) relative to the desired acetabular cup orientation. The information acquired and established in 31 may include the 3-axis distance between the landmarks and a center of rotation of the acetabulum, and an orientation of the cup 18 relative to these two landmarks. Other data that may be used is the skin thickness at the landmarks. The orientation of the cup 18 may be defined through an axis of the cup 18 normal to the plane in which lies the rim of the cup 18, the normal passing through the center of the cup 18. Other definitions of the cup orientation are contemplated as well.

In 32, with the desired acetabular cup orientation obtained in 31 relative to the pelvis (i.e., the landmarks and center of rotation), the required geometry of the visual guide 20 may be determined and this may include consideration of the type of cup implant 18 used. The geometry of the visual guide 20 is selected such that, once the cup impactor 10 and visual guide 20 are arranged in the manner shown in FIG. 1, with the light sources 24 being turned on, the selected landmarks will be targeted by the light beams C of the light sources 24. The spatial relation between the cup impactor 10/visual guide 20 and the pelvis A, based on the measurement taken in 31, ensure that only a proper alignment including the cup implant 18 in the acetabulum of the femur A, namely to the desired acetabular cup orientation, will result in the landmarks being lit up. Hence, the patient-specific visual guide 20 for cup impactor may be created based on the information found in step 31.

33 of method 30 is performed intra-operatively and is executed after the acetabulum has been resurfaced or when the acetabulum is ready to received the cup 18 therein. Hence, in 33, the cup impactor 10 has the cup 18 at its end in the manner shown in FIG. 1, for the cup 18 to be implanted. The cup impactor 10 also has the visual guide 20 thereon. In the embodiment of FIG. 1, the light sources 24 are turned on and the cup impactor 10 is positioned in the manner shown in FIG. 1, with the cup 18 seated in the acetabulum, but not yet impacted therein, thereby forming a spherical like-joint allowing rotations of the cup impactor 10, in two or three rotational degrees of freedom. At that moment, the operator is required to properly orient the impactor 10—i.e., rotate the impactor 10 in up to three degrees of freedom—while keeping the cup 18 seated in the acetabulum, until the light beams C illuminate the planned landmarks.

In the preparation of the pelvis leading to 33, it may be desired for the operator to place target stickers or to mark the soft tissue covering the planned landmarks to facilitate their subsequent targeting with the visual guide 20.

Once the landmarks are targeted by the visual guide 20 while the cup 18 is seated in the acetabulum and the operator is satisfied with the orientation and the alignment, the cup 18 may be impacted to desired orientation as identified at 34.

As mentioned previously, the sleeve 21 may include a prismatic joint. The prismatic joint of the sleeve 21 may help in confirming the proper orientation during the impacting until the cup 18 is implanted, considering that the cup 18 will move into engagement into the acetabulum and hence the visual guide 20 will change its position in the process. As such, the movement permitted by the prismatic joint of the sleeve 21 may be the equivalent of the impacting depth. Therefore, the operator may displace the visual guide 20 against the biasing mechanism to confirm the alignment of the light sources 24 once the impacting of the cup 18 has begun. Alternatively, the reverse process is considered as well, in which the operator in 33 may need to displace the sleeve 21 along the shaft 16 when the impacting has not begun, to align the visual guide 20 with the landmarks.

Still referring to FIG. 2, as an alternative to creating the cup impactor 10 with the patient-specific visual guide 20, a generic visual guide 20 may be used that is not specifically designed for the patient, using instead a patient-specific block. In FIG. 2, 35 is done instead of 32. 35 pertains to the creation of the patient-specific block. The patient-specific block is created as a function of the pre-operative acetabular cup orientation that has been determined in 31, using similar data, such as the spatial relation, the center of rotation of the acetabulum, the desired abduction and anteversion angles relative to the axis of the cup 18. The patient-specific block is a block featuring a surface that is contour-matching fabricated to sit perfectly on a given surface of the bone, based on the pre-operative planning of 31. Accordingly, by the high-accuracy interconnection between the patient-specific block and the bone when the patient-specific block is against the bone in complementary engagement, it is possible to have a visual guide (as 20 in FIG. 1) on the block at the precise location at which it would be on the cup impactor 10 in the desired alignment of 33 (knowing the manufacturers dimensions of cup impactors, etc).

Figure 3:
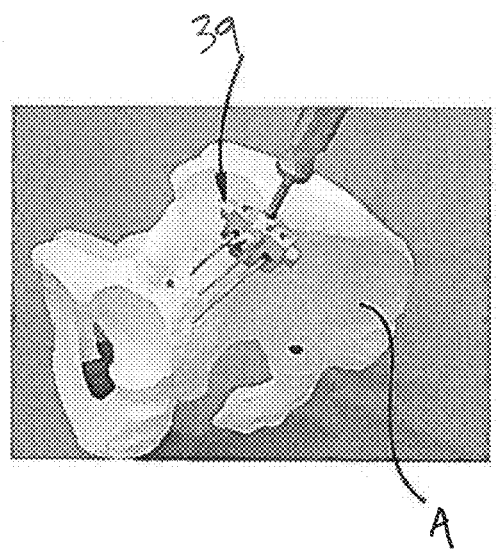
FIG. 3 is a perspective view of a block and Steinmann pins that may be used in part of the method of FIG. 2.

According to 36, intra-operatively, a temporary alignment target is created. This is done for instance by securing Steinmann pins and a target block on the pelvis, in a region in which the visual guide is predicted to target. Such an arrangement of Steinmann pins and target block is generally shown at 39 in FIG. 3, but other bone screws and targets may also be used. In an embodiment, the block is typically adjustable in position and orientation to ensure that it is aligned with the illumination field of the visual guide 20. Hence, with the temporary alignment target secured to the bone, the light beams C of the visual guide 20 on the patient-specific block are turned on to create targets. These targets may be marked by stickers, markers, etc.

Then, the method returns to 33 using the temporary alignment targets obtained in 36 instead of landmarks, and the generic visual guide 20 on the cup impactor 10. Accordingly, 35 and 36 suggest using an intra-operatively added target that is calibrated using a patient-specific block, the patient-specific block replicating the position of a generic visual guide on the cup impactor in the desired cup orientation. This alternate sequence does not rely on landmarks hidden by soft tissue.

For the sake of clarity additional embodiments are provided in the following figures. The additional embodiments have similarities with the embodiment of FIGS. 1-3, whereby like elements will bear like reference numerals.

Figure 4:
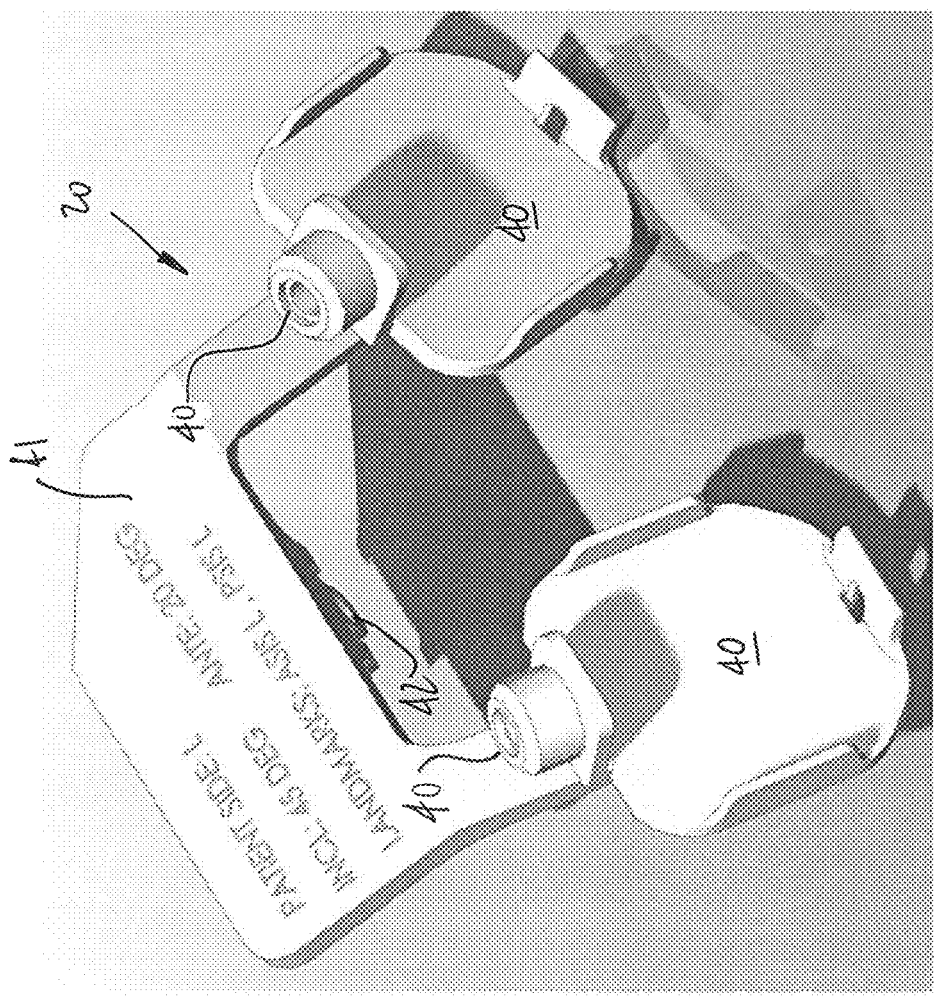
FIG. 4 is a perspective view of an embodiment of the visual guide of FIG. 1 in accordance with the present disclosure.

Referring to FIG. 4, an embodiment of the visual guide 20. The visual guide 20 is patient specific, as fabricated based on 31 and 32 of the method 30 of FIG. 2. The visual guide 20 in FIG. 4 has a pair of housings 40 conceived for the releasable connection of light sources therein. The housings 40 are interconnected to the cup impactor 10 by way of a body 41 and connector 42 interfacing the body 41 to the cup impactor 10.

The embodiment of the visual guide 20 is said to be patient specific, in that the geometry between the housings 40 and the connector 42 is shaped based on the patient's anatomy through steps 31 and 32 of FIG. 2. The housings 40 enable the use of generic light sources that can be snap-fitted to the visual guide 20, and subsequently be reused in other procedures (with adequate sterilization, etc).

Figure 5B:
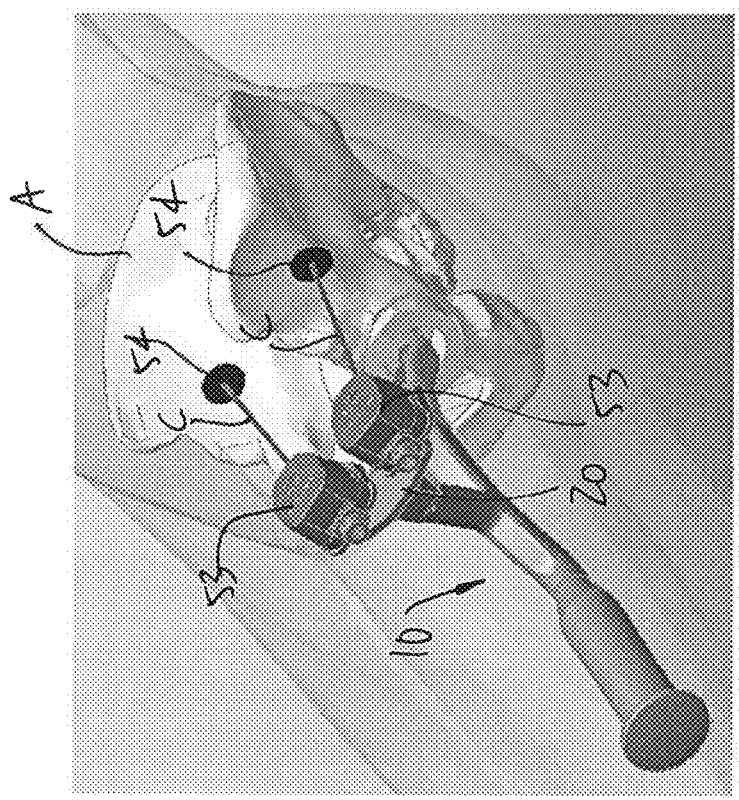
FIGS. 5A-5D illustrate a method of using a cup impactor with a patient specific block in accordance with the method of FIG. 2 of the present disclosure.
Figure 5A:
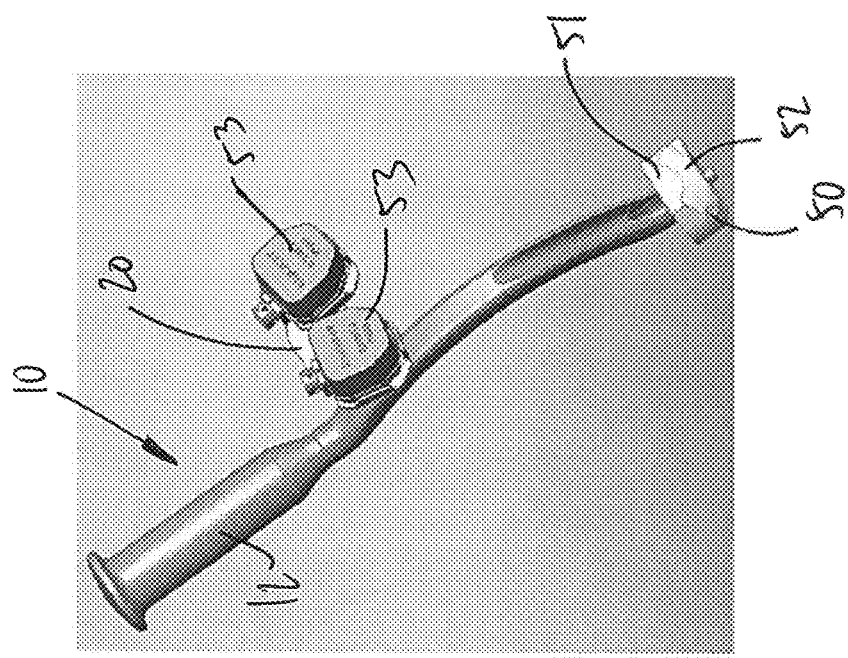

Referring now to FIGS. 5A to 5D, a sequence of steps is illustrated and is representative of steps 31, 35, 36, 33 and 34 of the method 30 of FIG. 2. As shown in FIG. 5A, a patient specific block 50 is used as a result of 31 and 35. The patient specific block 50 is devised to be received in the acetabulum in a single alignment orientation, because of the patient specific contour flange 51 (or like projection) surrounding the frusto-spherical portion 52. The cup impactor 10 has its cup coupler 14 in the patient specific block 50. Accordingly, when the cup impactor 10 is coupled to the pelvis A in the manner shown in FIG. 5B, with the patient specific block 50 in the single alignment orientation, the cup impactor 10 is aligned for implanting the cup in the desired acetabular cup orientation.

Figure 5D:
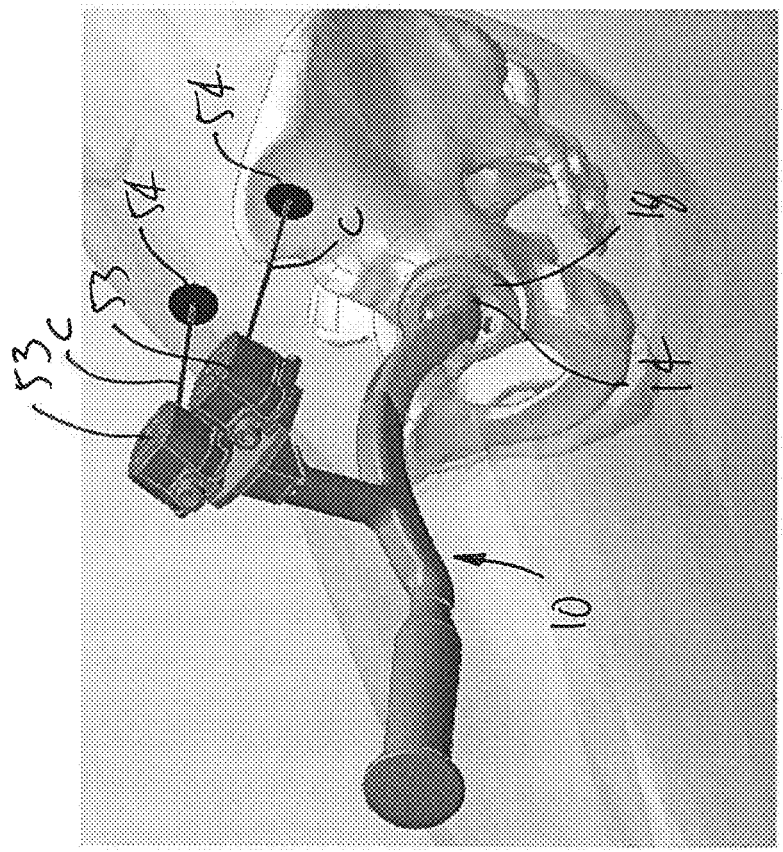
Figure 5C:
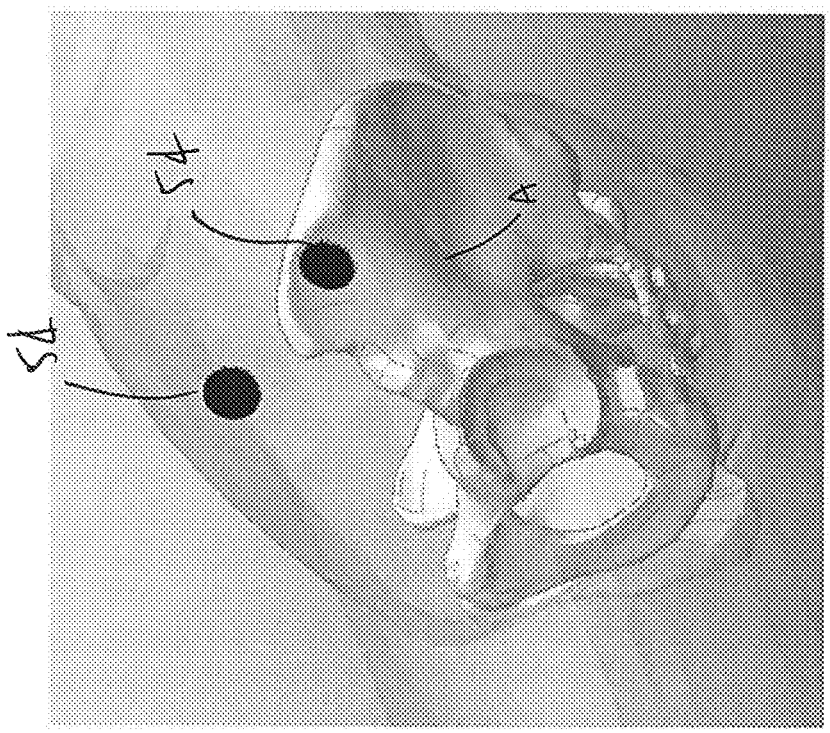

Still as in FIG. 5B, light sources 53 in a generic visual guide 20 may be used to lit up two unplanned and/or arbitrary landmarks on the patient, and stickers 54 or temporary marking may be used to identify the landmarks for subsequent use, as in FIG. 5C. Referring to FIG. 5D, the cup impactor 10 may then be used with the cup 18 at its end to impact the cup 18 into the acetabulum, after having removed the patient specific block 50. The stickers 54 are used in conjunction with the light beams to guide the operator in keeping the cup impactor 10 aligned during impaction.

Figure 6B:
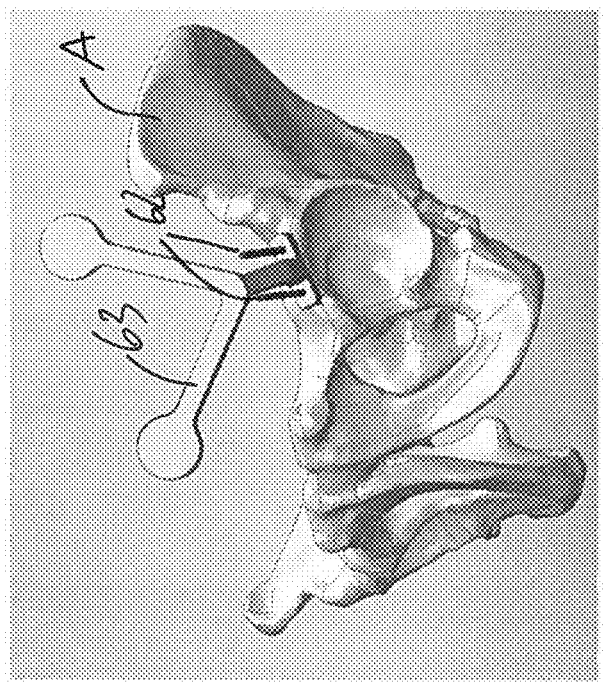
FIGS. 6A-6D illustrate a method of using a cup impactor with a patient specific block and a patient specific visual guide in accordance with the method of FIG. 2 of the present disclosure.
Figure 6A:
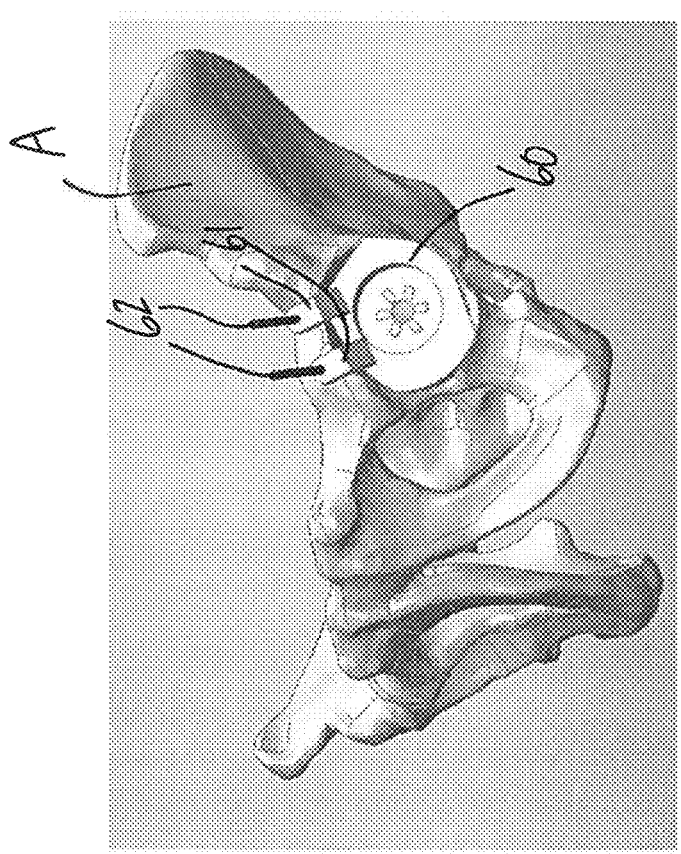

Referring now to FIGS. 6A to 6D, a sequence of steps is illustrated and is representative of steps 31-34, and 35-36 of the method 30 of FIG. 2, with the creating of a patient specific visual guide 20 and of a patient specific block 60. As shown in FIG. 6A, the patient specific block 60 is used as a result of 31 and 35. The patient specific block 60 is devised to be received in the acetabulum in a single alignment orientation, because of the patient specific contour surrounding a frusto-spherical portion. The patient specific block 60 further comprises a pair of guides 61 for guiding the positioning of pins 62 in the pelvis A, as in FIG. 6A. The spacing between the pins 62 is predetermined based on the geometry of a generic target board 63.

Figure 6D:
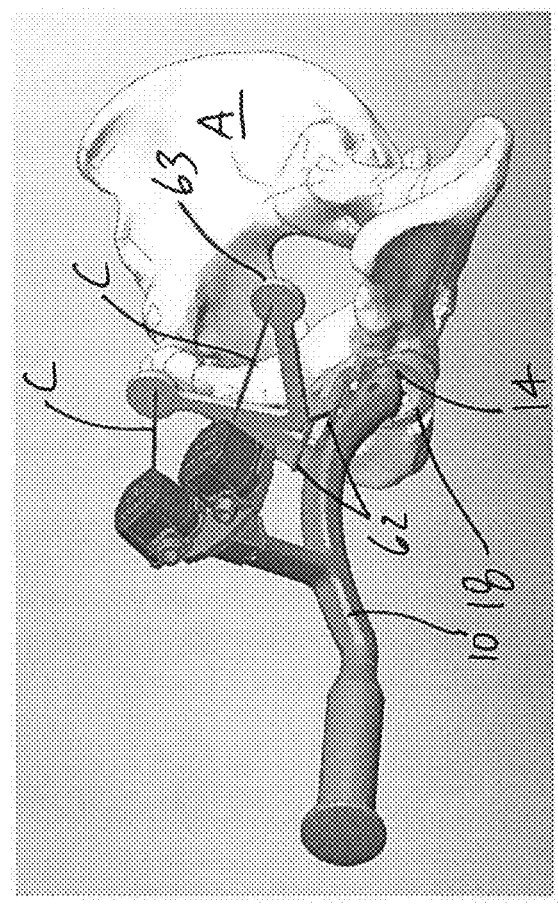
Figure 6C:
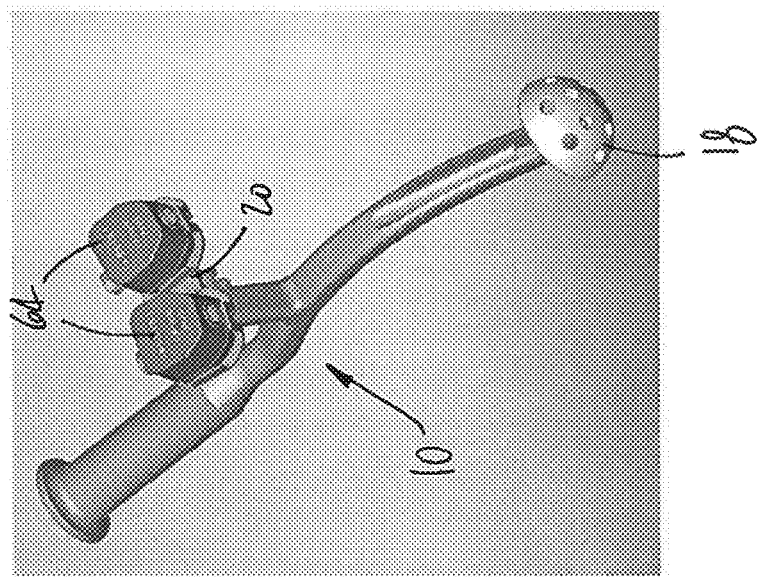

Referring to FIGS. 6C and 6D, the cup impactor 10 may then be used with the cup 18 at its end to impact the cup 10 into the acetabulum, with the patient specific visual guide 20 having light sources 64 used to lit up the two targets of the target board 63. The patient specific visual guide 20 may result from the steps 31 and 32 knowing the geometry of the target board 63 and its pre-planned orientation on the pelvis A. The orientation of the cup impactor 10 is adjusted with the cup 18 in the acetabulum until the light emitted by the light sources 64 is on the targets, at which point the cup 18 will be in the desired acetabular cup orientation.

Referring now to FIGS. 7A to 7C, a sequence of steps is illustrated and is representative of steps 31, 35, 36, 33 and 34 of the method 30 of FIG. 2. As shown in FIG. 7A, a patient specific block 70 is used as a result of 31 and 35. The patient specific block 70 is devised to be received in the acetabulum in a single alignment orientation, because of the patient specific contour flange 71 (or like projection) projecting from the frusto-spherical portion 72. The patient specific block 70 further comprises an arm 73 having a pin guide 74 at its end, the arm 73 being sized and the pin guide 74 being oriented such that a pin 75 may be connected to a predetermined landmark of the pelvis, such as the ASIS. As shown in FIG. 7C, the cup impactor 10 with cup 18 at its end may then use the pin 75 as visual guide or physical guide (with a sleeve 76) to remain in a desired orientation for the cup 18 to be implanted in its desired acetabular cup orientation. The sleeve 76 acts as a visual guide as it may not actually touch the pin 75 threaded through it. The pin 75 acts as a pair of landmarks, as it has an orientation and a position that result in the cup impactor 10 having a single possible orientation when guided by the pin 75 and seated in the acetabulum via the cup 18.

While the methods and systems described herein have been described and shown with reference to particular steps performed in a particular order, it will be understood that these steps may be combined, subdivided or reordered to form an equivalent method without departing from the teachings of the present invention. Accordingly, the order and grouping of the steps is not a limitation of the present invention.

Modifications and improvements to the above-described embodiments of the present invention may become apparent to those skilled in the art. The foregoing description is intended to be exemplary rather than limiting. For example, the landmarks may be on other parts of the body or on components other than the ones described, provided they remain during use in a relatively fixed relation relative to the pelvis A. The scope of the present invention is therefore intended to be limited solely by the scope of the appended claims.

The invention claimed is:

1. A method for orienting an acetabular cup prior to impacting in an acetabulum of a pelvis, comprising:

obtaining a cup impactor with a visual guide thereon at a location based on pre-operative planning specific to the patient, the visual guide emitting simultaneously at least two light beams;

releasably connecting an acetabular cup to an end of the cup impactor;

seating the cup at the end of the cup impactor in the acetabulum;

aligning the visual guide with at least two landmarks on the pelvis planned in the pre-operative planning specific to the patient by rotating the cup impactor with the cup seated in the acetabulum until a first of the light beams points a first of the landmarks on the pelvis, and a second of the light beams points a second of the landmarks on the pelvis separate from the first of the landmarks, the first and the second of the light beams being non-parallel to one another; and when the visual guide is aligned, impacting the cup into the acetabulum with the cup impactor.

2. The method according to claim 1, wherein impacting the cup comprises translating the visual guide along the cup impactor to verify the impacting.

3. The method according to claim 1, further comprising, prior to seating the cup in the acetabulum:

obtaining a patient specific block adapted to be received in the acetabulum in a single possible orientation based on the pre-operative planning specific to the patient, releasably connecting the patient specific block to the end of the cup impactor, seating the patient block at the end of the cup impactor in the acetabulum, and creating the at least two landmarks with the visual guide on the cup impactor.

4. The method according to claim 3, wherein creating the at least two landmarks with the visual guide comprises manually marking the at least two landmarks on the pelvis for subsequent use.

5. The method according to claim 4, wherein manually marking comprises at least one of securing stickers on and marking with ink the landmarks.

6. The method according to claim 1, further comprising, prior to seating the cup in the acetabulum:

obtaining a patient specific block adapted to be received in the acetabulum in a single possible orientation based on the pre-operative planning specific to the patient, and creating the at least two landmarks with the patient specific block.

7. The method according to claim 6, wherein creating the at least two landmarks with patient specific block comprises positioning at least one pin with the patient specific block for subsequent use in aligning the visual guide.

8. The method according to claim 7, further comprising positioning two of said pin, and positioning a target board on the pins, wherein aligning the visual guide with at least two landmarks comprises aligning the visual guide with the at least two landmarks being on the target board.

* * * * *